United States Patent
Nandra et al.

(10) Patent No.: US 10,555,917 B1
(45) Date of Patent: Feb. 11, 2020

(54) METHODS OF TREATING A NEUROLOGICAL OR PSYCHIATRIC DISORDER

(71) Applicants: Guriqbal S. Nandra, Chicago, IL (US); Irvin M. Wiesman, Chicago, IL (US)

(72) Inventors: Guriqbal S. Nandra, Chicago, IL (US); Irvin M. Wiesman, Chicago, IL (US)

(73) Assignee: BNIW Ventures LLC., Chicago, IL (US)

( * ) Notice: Subject to any disclaimer, the term of this patent is extended or adjusted under 35 U.S.C. 154(b) by 0 days.

(21) Appl. No.: 16/507,488

(22) Filed: Jul. 10, 2019

Related U.S. Application Data

(63) Continuation-in-part of application No. 15/998,635, filed on Aug. 16, 2018, now abandoned.

(51) Int. Cl.
| | |
|---|---|
| *A61K 31/7028* | (2006.01) |
| *A61K 31/496* | (2006.01) |
| *A61K 31/44* | (2006.01) |
| *A61K 31/40* | (2006.01) |
| *A61K 31/19* | (2006.01) |
| *A61K 31/13* | (2006.01) |
| *A61K 31/135* | (2006.01) |
| *A61K 9/00* | (2006.01) |
| *A61K 31/7076* | (2006.01) |
| *A61K 38/22* | (2006.01) |
| *A61K 31/352* | (2006.01) |
| *A61K 31/381* | (2006.01) |
| *A61K 31/455* | (2006.01) |
| *A61K 31/05* | (2006.01) |
| *A61K 31/155* | (2006.01) |
| *A61K 31/4375* | (2006.01) |
| *A61K 31/12* | (2006.01) |
| *A61K 31/426* | (2006.01) |
| *A61K 45/06* | (2006.01) |
| *A61K 38/20* | (2006.01) |

(52) U.S. Cl.
CPC ......... *A61K 31/135* (2013.01); *A61K 9/0019* (2013.01); *A61K 31/05* (2013.01); *A61K 31/12* (2013.01); *A61K 31/155* (2013.01); *A61K 31/352* (2013.01); *A61K 31/381* (2013.01); *A61K 31/426* (2013.01); *A61K 31/4375* (2013.01); *A61K 31/455* (2013.01); *A61K 31/7076* (2013.01); *A61K 38/204* (2013.01); *A61K 38/2264* (2013.01); *A61K 45/06* (2013.01)

(58) Field of Classification Search
CPC ............. A61K 31/7028; A61K 31/496; A61K 31/419; A61K 31/561; A61K 31/676
USPC ............ 514/25, 253.06, 356, 419, 561, 676
See application file for complete search history.

(56) References Cited

U.S. PATENT DOCUMENTS

| | | | | |
|---|---|---|---|---|
| 2007/0287753 A1* | 12/2007 | Charney | ............... | A61K 9/0019 514/647 |
| 2018/0177744 A1* | 6/2018 | Jay | ....................... | A61K 31/135 |
| 2018/0256534 A1* | 9/2018 | Erickson | ............... | A61K 31/135 |

FOREIGN PATENT DOCUMENTS

| WO | WO-2018195318 A1 * | 10/2018 | ........... A61K 9/7084 |
|---|---|---|---|
| WO | WO-2019094596 A1 * | 5/2019 | ............. A61K 31/35 |

* cited by examiner

*Primary Examiner* — Raymond J Henley, III
(74) *Attorney, Agent, or Firm* — Dennemeyer & Associates, LLC

(57) ABSTRACT

Provided are methods of treating a neurological or psychiatric disorder in a subject in need thereof, comprising: administering to the subject a therapeutically effective amount of ketamine or a pharmaceutically acceptable salt thereof in combination with an amount of one or more compounds effective to increase the level of nicotinamide adenine dinucleotide ($NAD^+$) in the subject.

25 Claims, No Drawings

METHODS OF TREATING A NEUROLOGICAL OR PSYCHIATRIC DISORDER

Provided herein are methods of treating a neurological or psychiatric disorder in a subject in need thereof.

Ketamine is a nonbarbiturate general anesthetic chemically designated dl 2-(2-chlorophenyl)-2-(methylamino)cyclohexan-1-one.

Esketamine is the S-isomer, i.e., (S)-ketamine or S(+)-ketamine. In addition to its anesthetic effects, esketamine shows properties of being a rapid-acting antidepressant.

Arketamine, also (R)-ketamine or (R)-(−)-ketamine, is the (R)-(−) enantiomer of ketamine. Arketamine is biologically active; however, it is less potent as an NMDA receptor antagonist and anesthetic and thus has not been approved or marketed for clinical use as an enantiopure drug.

NADH stands for "nicotinamide adenine dinucleotide (NAD)+hydrogen (H)." This chemical occurs naturally in the body and plays a role in the chemical process that generates energy.

There is a significant, unmet need for methods for treating a neurological or psychiatric disorder. The present disclosure fulfills these and other needs, as evident in reference to the following disclosure.

Provided are methods of treating a neurological or psychiatric disorder in a subject in need thereof, comprising: administering to the subject a therapeutically effective amount of ketamine or a pharmaceutically acceptable salt thereof in combination with an amount of one or more compounds effective to increase the level of nicotinamide adenine dinucleotide ($NAD^+$) in the subject.

These and other aspects of the invention will be apparent upon reference to the following detailed description. To this end, various references are set forth herein which describe in more detail certain background information, procedures, compounds, and/or compositions, and are each hereby incorporated by reference in their entirety.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Also, as used in this specification and the appended claims, the singular forms "a," "an," and "the" include plural referents unless the content clearly dictates otherwise.

As used herein, "co-administer" and "co-administration" and variants thereof mean the administration of at least two drugs to a patient either subsequently, simultaneously, or consequently proximate in time to one another (e.g., within the same day, or week or period of 30 days, or sufficiently proximate that each of the at least two drugs can be simultaneously detected in the blood plasma). When co-administered, two or more active agents can be co-formulated as part of the same composition or administered as separate formulations. This also may be referred to herein as "concomitant" administration or variants thereof.

As used herein, "adjusting administration", "altering administration", "adjusting dosing", or "altering dosing" are all equivalent and mean tapering off, reducing or increasing the dose of the substance, ceasing to administer the substance to the patient, or substituting a different active agent for the substance.

As used herein, "administering to a patient" refers to the process of introducing a composition or dosage form into the patient via an art-recognized means of introduction.

As used herein the term "disorder" is intended to be generally synonymous, and is used interchangeably with, the terms "disease," "syndrome," and "condition" (as in medical condition), in that all reflect an abnormal condition of the human or animal body or of one of its parts that impairs normal functioning, is typically manifested by distinguishing signs and symptoms.

As used herein, a "dose" means the measured quantity of an active agent to be taken at one time by a patient.

As used herein, "dosing regimen" means the dose of an active agent taken at a first time by a patient and the interval (time or symptomatic) at which any subsequent doses of the active agent are taken by the patient. The additional doses of the active agent can be different from the dose taken at the first time.

As used herein, "effective amount" and "therapeutically effective amount" of an agent, compound, drug, composition or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "patient" or "individual" or "subject" means a mammal, including a human, for whom or which therapy is desired, and generally refers to the recipient of the therapy.

As used herein, "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"Pharmacologically active" (or simply "active") as in a "pharmacologically active" (or "active") derivative or analog, refers to a derivative or analog having the same type of pharmacological activity as the parent compound and approximately equivalent in degree.

The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, a "product" or "pharmaceutical product" means a dosage form of an active agent plus published material, and optionally packaging.

As used herein, "treating" or "treatment" refers to therapeutic applications to slow or stop progression of a disorder, prophylactic application to prevent development of a disorder, and/or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

As used herein, the term "NAD precursor" refers to molecules that can be converted/synthesized in vivo into NAD. NAD precursors are known in the art and include, for example, NR and derivatives and analogs thereof (e.g., nicotinoyl ribosides), as well as molecules that can be converted/synthesized in vivo into NR. For example, certain NAD precursors are discussed in, e.g., WO 2006/116322, WO 2015014722, WO 2015186114, WO 2015186068, WO 2016014927, WO 2016/149277, WO 2016049236, WO 2015066382, U.S. Pat. No. 9,408,834, and Kulikova et al., Journal of Biological Chemistry (2015), 290(45), 27124-27137, each of which is incorporated by reference herein.

Provided is a method of treating a neurological or psychiatric disorder in a subject in need thereof, comprising: administering to the subject a therapeutically effective amount of ketamine or a pharmaceutically acceptable salt thereof in combination with an amount of one or more compounds effective to increase the level of nicotinamide adenine dinucleotide ($NAD^+$) in the subject.

In some embodiments, the method for comprises monitoring the subject for neurological deficits. In some embodiments, monitoring determines cognitive functioning and/or pathology.

In some embodiments, the neurological or psychiatric disorder is chosen from chronic traumatic encephalopathy, dementia, and neurodegenerative disease. In some embodiments, the neurological or psychiatric disorder is chronic traumatic encephalopathy. In some embodiments, the neurological or psychiatric disorder is dementia.

In some embodiments, the neurodegenerative disease is chosen from amyotrophic lateral sclerosis, Alzheimer's Disease, Parkinson's Disease, and Huntington's Disease. In some embodiments, the neurodegenerative disease is amyotrophic lateral sclerosis. In some embodiments, the neurodegenerative disease is Alzheimer's Disease.

In some embodiments, the neurodegenerative disease is Alzheimer's Disease and the administration results in inhibiting progression from Mild Cognitive Impairment (MCI) or pre-MCI to dementia stage of Alzheimer's Disease in the subject. In some embodiments, the neurodegenerative disease is Alzheimer's Disease and the administration results in inhibiting progression to dementia stage of Alzheimer's Disease (AD) in a subject with Down Syndrome or a subject with familial AD mutation.

In some embodiments, the methods result in an increase and/or stimulation of activation of BDNF (brain derived neurotrophic factor). In some embodiments, the methods result in stimulation of neurogenesis. In some embodiments, the methods result in a promotion of neuroplasticity. In some embodiments, the methods may decrease the level of tau, amyloid and/or "misfolded" protein deposits in the brain and/or nervous system of the subject.

In some embodiments, the ketamine or a pharmaceutically acceptable salt thereof is administered as esketamine or a pharmaceutically acceptable salt thereof. In some embodiments, the ketamine or a pharmaceutically acceptable salt thereof is administered as arketamine or a pharmaceutically acceptable salt thereof. In some embodiments, the ketamine or a pharmaceutically acceptable salt thereof is administered as a pharmaceutically acceptable salt. In some embodiments, the pharmaceutically acceptable salt is the hydrochloride salt.

In some embodiments, the one or more compounds effective to increase the level of nicotinamide adenine dinucleotide ($NAD^+$) in the subject is $NAD^+$.

In some embodiments, the one or more compounds effective to increase the level of nicotinamide adenine dinucleotide ($NAD^+$) in the subject is one or more $NAD^+$ precursors. In some embodiments, the one or more $NAD^+$ precursors is chosen from nicotinic acid, nicotinamide, nicotinamide mononucleotide (NMN), nicotinamide riboside (NR), or a salt thereof. In some embodiments, the one or more NAD+ precursors is one or more nicotinamide mononucleotide derivative as described, e.g., in U.S. Pat. No. 9,919,003.

In some embodiments, the one or more compounds effective to increase the level of nicotinamide adenine dinucleotide ($NAD^+$) in the subject is one or more NAD boosters. In some embodiments, the one or more NAD boosters is chosen from tryptophan, niacin, N-formylkynurenine, quinolinic acid, and nicotinamide riboside kinase (NRK).

In some embodiments, the one or more compounds effective to increase the level of nicotinamide adenine dinucleotide ($NAD^+$) in the subject is an agent that increases the activity of one or more enzymes involved in $NAD^+$ biosynthesis. In some embodiments, the one or more enzymes involved in $NAD^+$ biosynthesis is chosen from nicotinate phosphoribosyl transferase 1 (NPT1), pyrazinamidase/nicotinamidase 1 (PNC1), nicotinic acid mononucleotide adenylyltransferase 1 (NMA1), nicotinic acid mononucleotide adenylyltransferase 2 (NMA2), nicotinamide N-methyltransferase (NNMT), nicotinamide phosphoribosyl transferase (NAMPT or NAMPRT), nicotinate/nicotinamide mononucleotide adenylyl transferase 1 (NMNAT-1), and nicotinamide mononucleotide adenylyl transferase 2 (NMNAT-2).

In some embodiments, the one or more compounds effective to increase the level of nicotinamide adenine dinucleotide ($NAD^+$) in the subject is one or more compounds that induce NAD+ levels, independent of the stimulation of NAD+ synthesis or the inhibition of NAD+ usage. In some embodiments, the one or more compounds is chosen from activators of AMP activated kinase (AMPK). In some embodiments, the activators of AMP activated kinase is chosen 5-aminoimidazole-4-carboxamide-1-b-D-riboside, PT-1, A-769662 (Abbott), Adiponectin, Leptin, Ghrelin, Cannabinoids, alpha-lipoic acid, Interleukin-6 (IL-6), Resveratrol, Quercetin, Metformin, Berberine, Curcumine, Epigallocatechin-3-gallate (green tea), Thiazolidinediones, and Dinitrophenol (DNP).

In some embodiments, the subject is also administered vitamins, minerals, and/or supplements.

In some embodiments, the ketamine or a pharmaceutically acceptable salt thereof, is administered as a pharmaceutical composition comprising the ketamine or a pharmaceutically acceptable salt thereof, with one or pharmaceutically acceptable carriers or excipients.

In some embodiments, the one or more compounds effective to increase the level of nicotinamide adenine dinucleotide ($NAD^+$) is administered as a pharmaceutical composition comprising the one or more compounds, with one or pharmaceutically acceptable carriers or excipients.

The choice of excipient, to a large extent, depends on factors, such as the particular mode of administration, the effect of the excipient on the solubility and stability of the active ingredient, and the nature of the dosage form.

The pharmaceutical compositions provided herein may be provided in unit dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules and syringes. Unit dosage forms may be administered in fractions or multiples thereof. A multiple-dosage form is a plurality of identical unit-dosage forms packaged in a single container to be administered in segregated unit-dosage form.

These dosage forms can be prepared according to conventional methods and techniques known to those skilled in the art. The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science.

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl phydroxybenzates, thimerosal, benzalkonium chloride, benzethonium chloride, methyl- and propylparabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including alpha-cyclodextrin, beta-cyclodextrin, hydroxypropyl-beta-cyclodextrin, sulfobutylether-beta-cyclodextrin, and sulfobutylether 7-beta-cyclodextrin (CAPTISOL®, CyDex, Lenexa, Kans.).

The pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In certain embodiments, the pharmaceutical compositions are provided as ready-to-use sterile solutions. In certain embodiments, the pharmaceutical compositions are provided as sterile dry soluble products, including lyophilized powders and hypodermic tablets, to be reconstituted with a vehicle prior to use. In certain embodiments, the pharmaceutical compositions are provided as ready-to-use sterile suspensions. In certain embodiments, the pharmaceutical compositions are provided as sterile dry insoluble products to be reconstituted with a vehicle prior to use. In certain embodiments, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms. The pharmaceutical compositions may be formulated as a suspension, solid, semi-solid, or thixotropic liquid, for administration as an implanted depot.

In some embodiments, the ketamine or a pharmaceutically acceptable salt thereof or the one or more compounds is administered intravenously. In some embodiments, the ketamine or a pharmaceutically acceptable salt thereof or the one or more compounds is administered by infusion. In some embodiments, the ketamine or a pharmaceutically acceptable salt thereof or the one or more compounds is administered by intravenous bolus, as a continuous intravenous infusion, or a combination thereof. In some embodiments, the ketamine or a pharmaceutically acceptable salt thereof or the one or more compounds is administered as a single bolus initially, and then administered as a continuous infusion following the bolus. The rate of the infusion can be any rate, e.g., from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min.

In some embodiments, the infusions are administered once a week over a course of 2, 3, 4, 5, or 6 weeks. In some embodiments, the infusions are administered twice a week over a course of 2, 3, 4, 5, or 6 weeks. In some embodiments, the infusions are administered once or twice a week over a course of more than 6 weeks. In some embodiments, the infusions are administered over a course of 2, 3, 4, 5, or 6 weeks and then maintenance infusions are subsequently administered every month to every few months.

In some embodiments, the methods comprise initially administering the ketamine or a pharmaceutically acceptable salt thereof in combination with an amount of one or more compounds effective to increase the level of nicotinamide adenine dinucleotide (NAD+) in the subject by intravenous routes, such as by infusion, and subsequently administering ketamine or a pharmaceutically acceptable salt thereof, optionally in combination, with an amount of one or more compounds effective to increase the level of nicotinamide adenine dinucleotide (NAD+) in the subject by a route that is not intravenous. In some embodiments, both the ketamine or a pharmaceutically acceptable salt thereof and the one or more compounds are subsequently administered by a non-intravenous route. In some embodiments, only one of the ketamine or a pharmaceutically acceptable salt thereof or the one or more compounds is subsequently administered by a non-intravenous route and the other of the ketamine or a pharmaceutically acceptable salt thereof or the one or more compounds is subsequently administered by an intravenous route.

In some embodiments, the non-intravenous route is oral or topical.

In some embodiments, the non-intravenous route is oral. In some embodiments, the non-intravenous route is buccal, lingual, or sublingual administration.

In some embodiments, the ketamine or a pharmaceutically acceptable salt thereof is in the form of a tablet, solution, capsule, troche, lozenge, pastille, cachet, pellet, medicated chewing gum, granule, effervescent or non-effervescent powder or granule, emulsion, suspension, wafer, sprinkle, elixir, or syrup.

In some embodiments, the ketamine or a pharmaceutically acceptable salt thereof is administered as a pharmaceutical composition that further comprises one or more pharmaceutically acceptable carriers is chosen from binders, fillers, diluents, disintegrants, wetting agents, lubricants, glidants, coloring agents, dye-migration inhibitors, sweetening agents, and flavoring agents.

In some embodiments, the pharmaceutical composition comprising ketamine or a pharmaceutically acceptable salt thereof is formulated as a modified release dosage form.

In some embodiments, the pharmaceutical composition comprising ketamine or a pharmaceutically acceptable salt thereof is formulated as a delayed-, extended-, prolonged-, sustained-, pulsatile-, controlled-, accelerated- and fast-, targeted-, programmed-release, or gastric retention dosage form.

In some embodiments, the one or more compounds effective to increase the level of nicotinamide adenine dinucleotide (NAD+) is in the form of a tablet, solution, capsule, troche, lozenge, pastille, cachet, pellet, medicated chewing gum, granule, effervescent or non-effervescent powder or granule, emulsion, suspension, wafer, sprinkle, elixir, or syrup.

In some embodiments, the one or more compounds effective to increase the level of nicotinamide adenine dinucleotide (NAD+) is administered as a pharmaceutical composition that further comprises one or more pharmaceutically acceptable carriers is chosen from binders, fillers, diluents, disintegrants, wetting agents, lubricants, glidants, coloring agents, dye-migration inhibitors, sweetening agents, and flavoring agents.

In some embodiments, the pharmaceutical composition comprising one or more compounds effective to increase the level of nicotinamide adenine dinucleotide (NAD+) is formulated as a modified release dosage form.

In some embodiments, the pharmaceutical composition comprising one or more compounds effective to increase the level of nicotinamide adenine dinucleotide (NAD+) is formulated as a delayed-, extended-, prolonged-, sustained-, pulsatile-, controlled-, accelerated- and fast-, targeted-, programmed-release, or gastric retention dosage form.

In some embodiments, the non-intravenous route of administration is topical administration. In some embodiments, topical administration comprises (intra)dermal, conjuctival, intracorneal, intraocular, ophthalmic, auricular, transdermal, nasal, vaginal, uretheral, respiratory, or rectal administration.

In some embodiments, the pharmaceutical composition comprising the ketamine or a pharmaceutically acceptable salt thereof is formulated as an emulsion, solution, suspension, cream, gel, hydrogel, ointment, dusting powder, dressing, elixir, lotion, suspension, tincture, paste, foam, film, aerosol, irrigation, spray, suppository, bandage, or dermal patch.

In some embodiments, the pharmaceutical composition comprising the ketamine or a pharmaceutically acceptable salt thereof is formulated as liposomes, micelles, microspheres, nanosystems, and mixtures thereof.

In some embodiments, the pharmaceutical composition comprising the ketamine or a pharmaceutically acceptable salt thereof further comprises one or more pharmaceutically acceptable carriers is chosen from aqueous vehicles, water miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

In some embodiments, the pharmaceutical composition comprising the ketamine or a pharmaceutically acceptable salt thereof is administered topically by electroporation, iontophoresis, phonophoresis, sonophoresis and microneedle or needle-free injection.

In some embodiments, the pharmaceutical composition comprising the ketamine or a pharmaceutically acceptable salt thereof the pharmaceutical composition is administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas.

In some embodiments, the pharmaceutical composition comprising the ketamine or a pharmaceutically acceptable salt thereof is administered intranasally or by inhalation to the respiratory tract.

In some embodiments, the pharmaceutical composition comprising the ketamine or a pharmaceutically acceptable salt thereof is in the form of an aerosol or solution for delivery using a pressurized container, pump, spray, atomizer, or nebulizer, alone or in combination with a suitable propellant.

In some embodiments, the pharmaceutical composition comprising the ketamine or a pharmaceutically acceptable salt thereof in the form of a dry powder for insufflation, alone or in combination with an inert carrier such as lactose or phospholipids; and nasal drops.

In some embodiments, the pharmaceutical composition comprising the one or more compounds effective to increase the level of nicotinamide adenine dinucleotide (NAD+) is formulated as an emulsion, solution, suspension, cream, gel, hydrogel, ointment, dusting powder, dressing, elixir, lotion, suspension, tincture, paste, foam, film, aerosol, irrigation, spray, suppository, bandage, or dermal patch.

In some embodiments, the pharmaceutical composition comprising the one or more compounds effective to increase the level of nicotinamide adenine dinucleotide (NAD+) is formulated as liposomes, micelles, microspheres, nanosystems, and mixtures thereof.

In some embodiments, the pharmaceutical composition comprising the one or more compounds effective to increase the level of nicotinamide adenine dinucleotide (NAD+) further comprises one or more pharmaceutically acceptable carriers is chosen from aqueous vehicles, water miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

In some embodiments, the pharmaceutical composition comprising the one or more compounds effective to increase the level of nicotinamide adenine dinucleotide (NAD+) is administered topically by electroporation, iontophoresis, phonophoresis, sonophoresis and microneedle or needle-free injection.

In some embodiments, the pharmaceutical composition comprising the one or more compounds effective to increase the level of nicotinamide adenine dinucleotide (NAD+) is administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas.

In some embodiments, the pharmaceutical composition comprising the one or more compounds effective to increase the level of nicotinamide adenine dinucleotide (NAD+) is administered intranasally or by inhalation to the respiratory tract.

In some embodiments, the pharmaceutical composition comprising the one or more compounds effective to increase the level of nicotinamide adenine dinucleotide (NAD+) is in the form of an aerosol or solution for delivery using a pressurized container, pump, spray, atomizer, or nebulizer, alone or in combination with a suitable propellant.

In some embodiments, the pharmaceutical composition comprising the one or more compounds effective to increase the level of nicotinamide adenine dinucleotide (NAD+) is in the form of a dry powder for insufflation, alone or in combination with an inert carrier such as lactose or phospholipids; and nasal drops.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In some embodiments, the ketamine or pharmaceutically acceptable salt thereof will be administered as a subanesthetic dose. In some embodiments, a subanesthetic dose is less than 4.5 mg/kg. In some embodiments, a subanesthetic dose is less than 4 mg/kg. In some embodiments, a subanesthetic dose is less than 3 mg/kg. In some embodiments, a subanesthetic dose is less than 2 mg/kg. In some embodiments, a subanesthetic dose is less than 1 mg/kg. In some embodiments, a subanesthetic dose is less than 0.5 mg/kg.

In some embodiments, the one or more compounds effective to increase the level of nicotinamide adenine dinucleotide (NAD+) is administered as a supranormal dose. In some embodiments, a supranormal dose is sufficient to produce a level of NAD+ in excess of those levels normally found as the result of the body's natural production of NAD+ or that level induced by the administration of NAD+ alone.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. A method of treating a neurological or psychiatric disorder in a subject in need thereof, comprising: administering to the subject a therapeutically effective amount of ketamine or a pharmaceutically acceptable salt thereof in combination with an amount of one or more compounds effective to increase the level of nicotinamide adenine dinucleotide (NAD+) in the subject.

2. The method of claim 1, wherein the neurological or psychiatric disorder is chosen from chronic traumatic encephalopathy, dementia, and neurodegenerative disease.

3. The method of claim 2, wherein the neurological or psychiatric disorder is chronic traumatic encephalopathy.

4. The method of claim 2, wherein the neurological or psychiatric disorder is dementia.

5. The method of claim 2, wherein the neurodegenerative disease is chosen from amyotrophic lateral sclerosis, Alzheimer's Disease, Parkinson's Disease, and Huntington's Disease.

6. The method of claim 5, wherein the neurodegenerative disease is amyotrophic lateral sclerosis.

7. The method of claim 5, wherein the neurodegenerative disease is Alzheimer's Disease.

8. The method of claim 7, wherein the administration results in inhibiting progression from Mild Cognitive Impairment (MCI) or pre-MCI to dementia stage of Alzheimer's Disease in the subject.

9. The method of claim 7, wherein the administration results in inhibiting progression to dementia stage of Alzheimer's Disease (AD) in a subject with Down Syndrome or a subject with familial AD mutation.

10. The method of claim 1, wherein the ketamine or a pharmaceutically acceptable salt thereof is administered as esketamine or a pharmaceutically acceptable salt thereof.

11. The method of claim 1, wherein the ketamine or a pharmaceutically acceptable salt thereof is administered as arketamine or a pharmaceutically acceptable salt thereof.

12. The method of claim 1, wherein the ketamine or a pharmaceutically acceptable salt thereof is administered as a pharmaceutically acceptable salt.

13. The method of claim 12, wherein the pharmaceutically acceptable salt is the hydrochloride salt.

14. The method of claim 1, wherein the ketamine or a pharmaceutically acceptable salt thereof is administered intravenously.

15. The method of claim 1, wherein the one or more compounds effective to increase the level of nicotinamide adenine dinucleotide (NAD+) in the subject is NAD+.

16. The method of claim 1, wherein the one or more compounds effective to increase the level of nicotinamide adenine dinucleotide (NAD+) in the subject is one or more NAD+ precursors.

17. The method of claim 16, wherein the one or more NAD+ precursors is chosen from nicotinic acid, nicotinamide, nicotinamide mononucleotide (NMN), nicotinamide riboside (NR), or a salt thereof.

18. The method of any one of claim 1, wherein the one or more compounds effective to increase the level of nicotinamide adenine dinucleotide (NAD+) in the subject is one or more NAD boosters.

19. The method of claim 18, wherein the one or more NAD boosters is chosen from tryptophan, niacin, N-formylkynurenine, quinolinic acid, and nicotinamide riboside kinase (NRK).

20. The method of claim 1, wherein the one or more compounds effective to increase the level of nicotinamide adenine dinucleotide (NAD+) in the subject is an agent that increases the activity of one or more enzymes involved in NAD+ biosynthesis.

21. The method of claim 20, wherein the one or more enzymes involved in NAD+ biosynthesis is chosen from nicotinate phosphoribosyl transferase 1 (NPT1), pyrazinamidase/nicotinamidase 1 (PNC1), nicotinic acid mononucleotide adenylyltransferase 1 (NMA1), nicotinic acid mononucleotide adenylyltransferase 2 (NMA2), nicotinamide N-methyltransferase (NNMT), nicotinamide phosphoribosyl transferase (NAMPT or NAMPRT), nicotinate/nicotinamide mononucleotide adenylyl transferase 1 (NMNAT-1), and nicotinamide mononucleotide adenylyl transferase 2 (NMNAT-2).

22. The method of claim 1, wherein the one or more compounds effective to increase the level of nicotinamide adenine dinucleotide (NAD+) in the subject is one or more compounds that induce NAD+ levels, independent of the stimulation of NAD+ synthesis or the inhibition of NAD+ usage.

23. The method of claim 22, wherein the one or more compounds is chosen from activators of AMP activated kinase (AMPK).

24. The method of claim 23, wherein the activators of AMP activated kinase is chosen 5-aminoimidazole-4-carboxamide-1-b-D-riboside, PT-1, A-769662 (Abbott), Adiponectin, Leptin, Ghrelin, Cannabinoids, alpha-lipoic acid, Interleukin-6 (IL-6), Resveratrol, Quercetin, Metformin, Berberine, Curcumine, Epigallocatechin-3-gallate (green tea), Thiazolidinediones, and Dinitrophenol (DNP).

25. The method of claim 1, wherein the subject is also administered vitamins, minerals, and/or supplements.

* * * * *